United States Patent
Wu et al.

(10) Patent No.: US 8,852,667 B2
(45) Date of Patent: Oct. 7, 2014

(54) METHOD FOR PREPARATION OF BIOACTIVE GLASS COATINGS BY LIQUID PRECURSOR THERMAL SPRAY

(75) Inventors: Fang Wu, Sichuan (CN); Yanfeng Xiao, Sichuan (CN); Lei Song, Sichuan (CN); Xiaoguang Liu, Sichuan (CN); Yi Huang, Sichuan (CN); Tao Huang, Sichuan (CN); Jiamin Feng, Sichuan (CN)

(73) Assignee: Si Chuan University, Sichuan (CN)

( * ) Notice: Subject to any disclaimer, the term of this patent is extended or adjusted under 35 U.S.C. 154(b) by 342 days.

(21) Appl. No.: 13/318,925

(22) PCT Filed: Jul. 10, 2009

(86) PCT No.: PCT/CN2009/072712
§ 371 (c)(1),
(2), (4) Date: Nov. 4, 2011

(87) PCT Pub. No.: WO2010/135873
PCT Pub. Date: Dec. 2, 2010

(65) Prior Publication Data
US 2012/0058250 A1  Mar. 8, 2012

(30) Foreign Application Priority Data
May 27, 2009  (CN) .......................... 2009 1 0302658

(51) Int. Cl.
*A61L 33/00* (2006.01)
*C23C 18/12* (2006.01)
(Continued)

(52) U.S. Cl.
CPC ............. *C23C 4/121* (2013.01); *C23C 18/1258* (2013.01); *C03C 1/008* (2013.01); *C23C 18/1245* (2013.01); *C23C 18/1212* (2013.01);
(Continued)

(58) Field of Classification Search
USPC .......................... 427/2.1, 189, 190, 191, 195
See application file for complete search history.

(56) References Cited

U.S. PATENT DOCUMENTS 6,623,796 B1 * 9/2003 Van Steenkiste ............. 427/189
2002/0076501 A1 6/2002 Costantini et al.

FOREIGN PATENT DOCUMENTS

CN  1486751 A  4/2004
CN  1539512 A  10/2004
(Continued)

OTHER PUBLICATIONS

Vasiliev et al., Coatings of metastable ceramics deposited by solution-precursor plasma spray:1, Binary ZrO2—Al2O3 system, 2006, Acta Materialia, vol. 54, pp. 4913-4920.*
(Continued)

*Primary Examiner* — Dah-Wei D Yuan
*Assistant Examiner* — Andrew Bowman
(74) *Attorney, Agent, or Firm* — Caesar, Rivise, Bernstein, Cohen & Pokotilow, Ltd.

(57) ABSTRACT

The present invention belongs to the field of biomedical material, and is particularly related to a method of preparing bioactive glass coatings by liquid precursor thermal spray. The objective of the present invention is to overcome the shortcomings of the air plasma spraying where the powder feedstock preparation is complicated and time-consuming, and sol-gel or other wet chemistry method where the synthesized coating generally has thin coating thickness and with low production efficiency. Therefore, a new method is provided for preparation of bioactive glass coatings. In this method, organic and inorganic raw materials were first weighed in accordance with the chemical composition of bioactive glasses, and sol or suspension was prepared; then the sol or suspension was used as the feedstock for thermal spray, and was deposited on the biomedical materials substrate, at high temperature to form the bioactive glass coating. The invention possesses the following advantages: simple operation, less complicated procedures, synthesis with high efficiency, low production cost, suitable for industrial production, and so on. This method can be used to prepare bioactive glass coatings.

11 Claims, 4 Drawing Sheets

(51) Int. Cl.
  *C23C 4/12* (2006.01)
  *C03C 1/00* (2006.01)
  *C03C 4/00* (2006.01)
  *C03C 3/112* (2006.01)
  *A61L 27/32* (2006.01)
  *C03C 3/062* (2006.01)
  *C03C 3/097* (2006.01)

(52) U.S. Cl.
  CPC ............... *C03C 4/0007* (2013.01); *C03C 3/112* (2013.01); *A61L 27/32* (2013.01); *C03C 3/062* (2013.01); *C23C 18/1254* (2013.01); *C03C 3/097* (2013.01); *A61L 2420/02* (2013.01)
  USPC ............ 427/2.1; 427/189; 427/190; 427/191; 427/195

(56) References Cited

FOREIGN PATENT DOCUMENTS

| | | |
|---|---|---|
| CN | 1740372 A | 3/2006 |
| EP | 1806155 A2 | 7/2007 |
| JP | 200968067 A | 4/2009 |

OTHER PUBLICATIONS

Jaworski et al., Optimization of Dielectric Properties of Suspesion Plasma Sprayed Hydroxyapatite Coatings, 2007, Mat-wiss. u. Werkstofftech, vol. 38 No. 2, pp. 125-130.*
International Search Report for PCT/CN2009/072712 dated Mar. 11, 2010.

* cited by examiner

METHOD FOR PREPARATION OF BIOACTIVE GLASS COATINGS BY LIQUID PRECURSOR THERMAL SPRAY

FIELD OF INVENTION

The present invention belongs to the field of biomedical material, and is particularly related to a method of preparing bioactive glass coatings by liquid precursor thermal spray.

BACKGROUND OF THE INVENTION

Bioactive glass was first invented by Hench and collaborators at the University of Florida in 1971 (L. L. Hench, R. J. Splinter, W. C. Allen, J. Biomed. Mater. Res. Symp., 1971, (2):117~141). Bioactive glass not only possesses excellent bioactivity, but also has favorable bonding to bone and soft tissue. Furthermore, it holds long-term security and stability when being implanted into body as an artificial bone replacement material. Therefore, bioactive glasses have great potential in dental, orthopedic, otology, and restoration applications (L. L. Hench, Bioceramics, J. Am. Ceram. Soc., 1998, (81):1705~1728). At present, bioactive glasses have received the approval from the U.S. Food and Drug Administration (FDA). However, the inferior mechanical properties of bioactive glasses, such as high brittleness and low toughness, limit their usages. It is one of the main methods to improve medical implants' bioactivity by depositing bioactive glass coatings onto Ti and Ti-based alloys. It integrates the superior mechanical strength of the Ti and Ti-based alloys and the excellent bioactivity, biocompatibility, osteoconductivity and osteoinductivity of the bioactive glasses. Hence, bioactive glass coatings were widely used in clinical applications, such as bone replacement and restoration.

Bioactive glass coatings were deposited on Ti and Ti-based alloys by various methods, including: powder metallurgy sintering, acidic and alkali treatment, laser cladding, pulsed laser deposition, magnetron sputtering, electrophoretic deposition, sol-gel, air plasma spraying, etc. Among them, sol-gel and air plasma spraying are the most widely used and researched methods at present. In the sol-gel method, the organic alkoxide was firstly hydrolyzed, and then the inorganic salt solution was added to form the sol. After being aged for a period of time, the sol was coated on the pretreated Ti and Ti-based alloy substrates. The sol coated substrate was dried at a certain temperature, and then the coating-drying process was repeated for many times. Finally, the coated substrate was sintered at a certain temperature to form the bioactive glass coating (L. D. Piveteau, M. I. Girona, L. Schlapbach, et al., Materials Science: Materials in Medicine, 1999, (10): 161-167). Air plasma spraying is one kind of the thermal spray methods. In the air plasma spraying method, there are stringent requirements on the preparation of the powder feedstocks. At first, the bioactive glass powders or blocks were often prepared through melt-and-quench process or sol-gel process. Then, the powders or blocks were crushed, ball milled and sieved to obtain the feedstocks for air plasma spraying. Next, the obtained powder feedstocks were added into the special feeding device of the plasma spray system. The powder feedstocks were transported through the tube under pressure, to the powder nozzle near the plasma spray gun. Finally, the powder were spurted into the plasma flame directly, rapidly melted in the high temperature plasma flame, and deposited on the Ti and Ti-based alloys to form the bioactive glass coatings (T. M. Lee, E. Chang, et. al., Surface and Coatings Technology, 1996, (79):170-177).

Bioactive glass coatings prepared by the sol-gel method have the following advantages: low reaction temperature, easily controlled reaction process, high uniformity and purity, exact stoichiometric composition, readiness for modification, wide range of doping composition, high bioactivity. However, this method also has the following shortcomings: long process time, thin coating thickness (usually about 10 µm), easy to crack, low bonding strength between the coating and substrate, complicated procedures, low productivity, unsuitable for large-scale production. Currently, air plasma spraying is one of the most widely used methods domestically and internationally, and is also the only successfully used technique in commercial application so far. The bioactive glass coatings prepared by air plasma spraying possesses high deposition efficiency, controllable thickness and high bonding strength between the substrate and the coating. However, there are stringent requirements on the preparation of the bioactive glass powder feedstocks. The feedstocks were commonly prepared through melt-and-quench process. Firstly, all the oxide constituents were mixed together and melted at high temperature. Then, the mixture was quenched to form bioactive glass blocks or powders. Finally, the blocks or powders were crushed, ball milled and sieved to obtain the feedstocks for air plasma spraying. Since it is complicated and time-consuming, the process has low productivity and high cost.

SUMMARY OF THE INVENTION

The objective of the present invention is to overcome the shortcomings of the air plasma spraying where the powder feedstock preparation is complicated and time-consuming, and sol-gel or other wet chemistry method where the synthesized coating generally has thin coating thickness and with low production efficiency. Therefore, a new method is provided for preparation of bioactive glass coatings.

The method includes the following steps:

a. Preparation of liquid bioactive glass precursor.

b. Deposition and formation of bioactive glass coatings on the biomedical material substrates, using the liquid bioactive glass precursor for thermal spray.

Among them, the liquid bioactive glass precursor, mentioned in the above step a, is composed of the following components:

The sources (salts) of silicon, phosphorus, calcium, sodium, magnesium, aluminum, kalium and fluorine are measured according to the amount of starting oxides: $SiO_2$ 30-60 wt %, $P_2O_5$ 1-40 wt %, $CaO$ 20-45 wt %, $Na_2O$ 0-25 wt %, $MgO$ 0-20 wt %, $Al_2O_3$ 0-3 wt %, $K_2O$ 0-8 wt %, $CaF_2$ 0-15 wt %.

Ethyl alcohol and deionized water are measured according to the molar ratios of silicon:ethyl alcohol=1:2-5, and silicon:$H_2O$=1:4-8, respectively.

Deionized water is also measured according to the mass ratios of calcium:$H_2O$=1:1-2, sodium:$H_2O$=1:1-2, magnesium:$H_2O$=1:1-2, aluminum:$H_2O$=1:1.5-2, kalium:$H_2O$=1:3-5, and fluorine:$H_2O$=1:1-2, respectively.

Among them, the above bioactive glass precursor is prepared using the following process:

1. Mixing the silicon salt and ethyl alcohol and stirring them uniformly, and then adding the deionized water.

2. Adjusting the pH value to 1-3, the silicon salt is hydrolyzed to form sol, and the sol is stirred uniformly after it becomes completely pellucid.

3. Adding the sources of phosphorus and stirring the sol uniformly.

4. Adding the salts of calcium, sodium, magnesium, aluminum, kalium and fluorine to the deionized water. After being completely dissolved, they are added to the hydrolyzed sol. The acidic precursor of bioactive glass for thermal spray is manufactured after uniform stirring.

Among them, the above bioactive glass basic precursor is prepared using the following process:

1. Mixing the silicon salt and ethyl alcohol and stirring them uniformly, and then adding the deionized water.

2. Adjusting the pH value to 9-11, the silicon salt is hydrolyzed to form suspension, stirring the suspension uniformly after it becomes completely muddy.

3. Adding the phosphorus salt followed by 5-10 min stirring.

4. Adding the salts of calcium, sodium, magnesium, aluminum, kalium and fluorine into the deionized water. After being completely dissolved, they are added to the hydrolyzed suspension. The basic precursor of bioactive glass for thermal spray is manufactured after uniform stirring.

Among them, the above silicon salt is at least one of the following materials: tetraethyl orthosilicate, trimethyl silanol, triethyl silanol and silicon tetrachloride.

Among them, the above phosphorus salt is at least one of the following materials: triethyl phosphate, calcium phosphate, sodium phosphate, calcium hydrogen phosphate, monosodium phosphate, potassium phosphate and potassium hydrogen phosphate.

Among them, the above calcium salt is at least one of the following materials: calcium nitrate, calcium chloride, calcium bicarbonate, calcium sulfate, calcium bisulfate, calcium phosphate and calcium phosphate secondary.

Among them, the above sodium salt is at least one of the following materials: sodium nitrate, sodium chloride, sodium carbonate, sodium bicarbonate, sodium sulfate, sodium bisulfate, sodium phosphate and sodium hydrogen phosphate.

Among them, the above magnesium salt is at least one of the following materials: magnesium nitrate, magnesium chloride, magnesium bicarbonate, magnesium sulfate and magnesium hydrogen sulfate.

Among them, the above aluminum salt is at least one of the following materials: aluminum nitrate, aluminum chloride, aluminum sulfate and aluminum sulfate hydrogen.

Among them, the above kalium salt is at least one of the following materials: potassium nitrate, potassium chloride, potassium carbonate, potassium bicarbonate, potassium sulfate, potassium sulfate, potassium chlorate, sub-potassium chlorate, potassium phosphate and potassium hydrogen phosphate.

Among them, the above fluorine salt is at least one of the following materials: ammonium fluoride, ammonium hydrogen fluoride and hydrogen fluoride.

Among them, the optimized components in the above steps a is as follows: the silica salt (source of silicon) is tetraethyl orthosilicate, the phosphorus salt (source of phosphorus) is triethyl phosphate, the calcium salt (source of calcium) is calcium nitrate, the sodium salt (source of sodium) is sodium nitrate, the source of magnesium salt (source of magnesium) is magnesium nitrate, the aluminum salt (source of aluminum) is aluminum nitrate, the kalium salt (source of kalium) is potassium nitrate, the fluorine salt (source of fluorine) is ammonium fluoride.

Among them, the characteristics of the above method to prepare bioactive glass coating lies in: the thermal spray technique mentioned in the above step b is either plasma spraying, or high velocity oxygen fuel spraying, or electric arc spraying, or thermal explosion spraying, or oxyacetylene flame thermal spraying.

Among them, the above thermal spray technique in step b is plasma spraying. The liquid bioactive glass precursors are directly injected into the high temperature area in plasma flame center in a radial direction, in the form of linear jet flow through a 50-200 micrometer small diameter catheter.

Furthermore, the distance between the plasma gun and the biomedical materials substrate in the above step b is 10-25 cm. The plasma spray power in the above step b is 24-60 kW.

The above mentioned biomedical material substrate is biomedical titanium, biomedical titanium alloy, biomedical stainless steel, biomedical Co-based alloy, biomedical metal biomedical metallic composite, biomedical ceramic, or biomedical ceramic composite.

According to the invention, sol or suspension was firstly prepared though wet chemical method. Then, the sol or suspension was used as the spray feedstock, and transported into the plasma flame. The liquid feedstock would undergo a series of processes at high temperature: refining and breakup, evaporation, combustion, decomposition, melting, and so on. Finally, bioactive glass coatings are deposited on the biomedical material substrates. In this invention, the biomedical material substrate is biomedical titanium, biomedical titanium alloy, biomedical stainless steel, biomedical Co-based alloy, biomedical metal, biomedical metallic composite, biomedical ceramic, or biomedical ceramic composite. The selection of material should ensure it to withstand the high temperature introduced during the plasma spraying process.

In this invention, the silicon salts (sources of silicon) are not limited to tetraethyl orthosilicate, and should include trimethyl silanol, triethyl silanol, silicon tetrachloride, and other organic or inorganic materials that contain silicon. The phosphorus salts (sources of phosphorus) are not limited to triethyl phosphate, and should include calcium phosphate, sodium phosphate, calcium hydrogen phosphate, monosodium phosphate, potassium phosphate, potassium hydrogen phosphate, and other organic or inorganic materials that contain phosphorous. The calcium salts (sources of calcium) are not limited to calcium nitrate, and should include calcium chloride, calcium bicarbonate, calcium sulfate, calcium bisulfate, calcium phosphate, calcium phosphate secondary, and other inorganic materials that contain calcium. The sodium salts (sources of sodium) are not limited to sodium nitrate, and should include sodium chloride, sodium carbonate, sodium bicarbonate, sodium sulfate, sodium bisulfate, sodium phosphate, sodium hydrogen phosphate, and other inorganic materials that contain sodium. The magnesium salts (sources of magnesium) are not limited to magnesium nitrate, and should include magnesium chloride, magnesium bicarbonate, magnesium sulfate, magnesium hydrogen sulfate, and other inorganic materials that contain magnesium. The aluminum salts (sources of aluminum) are not limited to aluminum nitrate, and should include aluminum chloride, aluminum sulfate, aluminum sulfate hydrogen, and other aluminiferous inorganic materials that contain aluminum. The kalium salts (sources of kalium) are not limited to potassium nitrate, and should include potassium carbonate, potassium bicarbonate, potassium sulfate, potassium sulfate, potassium chlorate, sub-potassium chlorate, potassium phosphate, potassium hydrogen phosphate, and other inorganic materials that contain kalium. The fluorine salts (sources of fluorine) are not limited to ammonium fluoride, and should include ammonium hydrogen fluoride, hydrogen fluoride, and other inorganic materials that contain fluorine. The acids to adjust the pH value in the preparation of the acidic precursors are not limited to nitric acid, and should include hydrofluoric acid, hydrochloric acid, sulphuric acid, acetic acid, and other acids. The bases to adjust the pH value in the preparation of the basic precursors are not limited to ammonia solution, and should include sodium hydroxide, potassium hydroxide, and other basic solutions.

The invention integrates the advantages of both the air plasma spraying and sol-gel method and overcomes their shortcomings. This technique simplifies the tedious process steps and reduces the production cost in the preparation of powder feedstocks for powder plasma spraying. It also shortens the processing time and overcomes the drawback of thin coating thickness of sol-gel process. The invention possesses the following advantages: simple production procedures, high efficiency, and suitableness for industrial production.

Specifically, the plasma spraying can be carried out according to the following steps:

(1) Preparation of Liquid Precursor of Bioactive Glass a) Firstly, tetraethyl orthosilicate (TEOS), triethyl phosphate (TEP), calcium nitrate ($Ca(NO_3)_2.4H_2O$), sodium nitrate ($NaNO_3$), magnesium nitrate ($Mg(NO_3)_2.6H_2O$), aluminum nitrate ($Al(NO_3)_3.9H_2O$), potassium nitrate ($KNO_3$), and ammonium fluoride ($NH_4F$) are measured according to the composition of the bioactive glass, which is 30-60 wt % $SiO_2$, 1-40 wt % $P_2O_5$, 20-45 wt % CaO, 0-25 wt % $Na_2O$, 0-20 wt % MgO, 0-3 wt % $Al_2O_3$, 0-8 wt % $K_2O$, and 0-15 wt % $CaF_2$ in terms of the starting oxides, respectively. Ethyl alcohol and deionized water are measured according to the following molar ratios: TEOS:Ethyl alcohol (EtOH)=1:2-5, TEOS:$H_2O$=1:4-8. Deionized water are also measured according to the following mass ratios: $Ca(NO_3)_2.4H_2O$:$H_2O$=1:1-2, $NaNO_3$:$H_2O$=1:1-2, $Mg(NO_3)_2.6H_2O$:$H_2O$=1:1-2, $Al(NO_3)_3.9H_2O$:$H_2O$=1:1.5-2, $KNO_3$:$H_2O$=1:3-5, $NH_4F$:$H_2O$=1:1-2.

b) Mix the measured tetraethyl orthosilicate and ethyl alcohol under magnetic stirring with the rotation speed of 350-700 rpm. Add the deionized water after 5-10 min stirring.

c) Add $HNO_3$ to adjust the pH value to 1-3. Keep stirring for 10-20 minutes after the solution is completely pellucid.

Or:

d) Add $NH_3.H_2O$ to adjust the pH value to 9-11. Keep stirring for 10-20 minutes after the solution is completely muddy.

e) Add the triethyl phosphate and stirring for 5-10 minutes.

f) Add the measured calcium nitrate, sodium nitrate, magnesium nitrate, aluminum nitrate, potassium nitrate, ammonium fluoride to the deionized water. After being completely dissolved, they are added to the hydrolyzed sol or suspension. The bioactive glass precursor for plasma spray is manufactured after 20-30 min stirring.

(2) Transportation and Injection of the Liquid Bioactive Glass Precursor

The electronic peristaltic pump is used as the driving power for the transportation of the liquid precursor. The rotating speed of the peristaltic pump is adjusted to 5-20 rpm. The bioactive glass precursor is transported, in a catheter with a diameter of 3-8 mm, to the injector near the plasma gun. The injection system uses small diameter tube with a 50-200 µm diameter, which injects the bioactive glass precursors into the high temperature area of the plasma flame center, in the form of linear jet flow.

(3) Liquid Precursor Plasma Spraying and the Formation of the Bioactive Glass Coating The plasma spray power is adjusted to 24-60 kW. The distance between the plasma gun and the biomedical materials substrate is 10-25 cm. The number of spray passes is 5-15. The liquid bioactive glass precursors are prepared through step (1), and transported and injected through step (2), and injected into the high temperature plasma flame at a certain speed. The liquid feedstock would undergo a series of process at high temperature: refining and breakup of droplets, evaporation, combustion, decomposition, melting, etc. Finally, feedstock materials are deposited and bioactive glass coating is formed on the biomedical materials substrate.

Compared to the existing technologies, the present invention has the following beneficial effect:

1. The invention adopts thermal spray to prepare bioactive glass coating. The prepared sol and suspension feedstocks are directly deposited on the biomedical materials substrate to form a bioactive glass coating, by undergoing the high temperature processes of refining and breakup of droplets, evaporation, combustion, decomposition, melting, etc. Comparing with the sol-gel method, the invention reduces the long aging time, shortens the tedious heat treatment process, and improves the production efficiency.

2. The invention adopts the liquid sol or suspension as the thermal spray feedstocks. Comparing to the feedstock preparation for powder thermal spray, the invention reduces steps of high temperature melting and rapid cooling of the oxides in the preparation of the bioactive glass powder feedstocks. It also reduces the tedious procedures in the bulk or powder treatment, including crushing, ball milling, sieving, etc. The production efficiency is significantly improved and the cost of production is largely reduced. Also in the existing sol-gel method for preparation of bioactive glass coatings, sol must be prepared before the coating steps. However, in this invention, the feedstocks can be made into in either sol or suspension form, with improved conveniency and speed.

3. The invention adopts liquid precursor thermal spray to prepare bioactive glass coating. The prepared coatings are thicker than the sol-gel coatings. Their thickness can reach up to 100-300 µm and even higher. The thickness of the sol-gel coating is generally only 10-30 µm. Therefore, the production efficiency has been greatly improved and is suitable for industrial production.

4. Comparing with the sol-gel coatings, the coatings prepared by this invention have higher bonding strength, and will not crack. It is much less likely to introduce impurities during the process and the synthesized coating has high purity. The quality of the coating has been improved.

5. In this invention, the transportation device in the liquid precursor thermal spray process is either peristaltic pump or pressure tank. The liquid precursor is directly transported to the injection system through a catheter with a diameter of 3-8 mm. The injection system adopts a 50-200 µm small diameter tube, which directly inject the precursors into the high temperature area. Comparing with the pneumatic powder conveying device in powder thermal spray, the transportation device for the liquid precursor has the following advantages: simple equipment, easy operation, and precise flow control. It can further improve the production efficiency and reduce production costs.

DETAILED DESCRIPTION OF PREFERRED EMBODIMENTS

The technical solution of the invention is as follows:

According to the invention, liquid precursors was firstly prepared though wet chemical method. Then, the liquid precursor was used as the spray feedstock, and transported into the plasma flame. The liquid feedstock would undergo a series of processes at high temperature: refining and breakup, evaporation, combustion, decomposition, melting, and so on. Finally, bioactive glass coatings are deposited on the biomedical material substrates. In this invention, the biomedical material substrate is biomedical titanium, biomedical titanium alloy, biomedical stainless steel, biomedical Co-based alloy, biomedical metal, biomedical metallic composite, biomedical ceramic, or biomedical ceramic composite. The selection of material should ensure it to withstand high temperature introduced during the plasma spraying process.

The liquid bioactive glass precursors in this invention are made up from the components with the following compositions:

The sources of silicon, phosphorus, calcium, sodium, magnesium, aluminum, potassium nitrate, and fluorine are measured according to the following oxide compositions: 30-60 wt % $SiO_2$, 1-40 wt % $P_2O_5$, 20-45 wt % CaO, 0-25 wt % $Na_2O$, 0-20 wt % MgO, 0-3 wt % $Al_2O_3$, 0-8 wt % $K_2O$, and 0-15 wt % $CaF_2$, respectively.

Ethyl alcohol and deionized water are measured according to the following molar ratios: source of silicon (silicon salt): ethyl alcohol (EtOH)=1:2-5, source of silicon (silicon salt): $H_2O$=1:4-8.

Deionized water IS also measured according to the following mass ratios: source of calcium (calcium salt):$H_2O$=1:1-2, source of sodium (sodium salt):$H_2O$=1:1-2, source of magnesium (magnesium salt):$H_2O$=1:1-2, source of aluminum (aluminum salt):$H_2O$=1:1.5-2, source of potassium (potassium salt):$H_2O$=1:3-5, source of fluorine (fluorine salt): $H_2O$=1:1-2.

Acidic precursors for bioactive glasses with above compositions can be prepared according to the following procedures:

(1) Mix the measured and ethyl alcohol, stir them uniformly, add the deionized water;

(2) Adjust the pH value to 1-3, the source of silicon (silicon salt) will be hydrolyzed to form a sol, keep stirring after the solution becomes completely pellucid;

(3) Add the source of phosphorous (phosphorous salt) and stir them uniformly;

(4) Add the measured sources of calcium, sodium, magnesium, aluminum, potassium nitrate, and fluorine to the deionized water. After being completely dissolved, they are added to the hydrolyzed sol or suspension. The acidic precursor of bioactive glasses for thermal spray is manufactured after stirring uniformly.

Basic precursors for bioactive glasses with above compositions can be prepared according to the following procedures:

(1) Mix the measured and ethyl alcohol, stir them uniformly, add the deionized water;

(2) Adjust the pH value to 9-11, the source of silicon (silicon salt) will be hydrolyzed to form a suspension, keep stirring after the solution becomes completely muddy;

(3) Add the phosphorus salt followed by 5-10 min stirring;

(4) Add the measured sources of calcium, sodium, magnesium, aluminum, potassium nitrate, and fluorine to the deionized water. After being completely dissolved, they are added to the hydrolyzed sol or suspension. The basic precursor of bioactive glasses for thermal spray is manufactured after stirring uniformly.

Among them, the source of silicon (silicon salt) is at least one of the following materials: tetraethyl orthosilicate, trimethyl silanol, triethyl silanol and silicon tetrachloride; the source of phosphorus (phosphorus salt) is at least one of the following materials: triethyl phosphate, calcium phosphate, sodium phosphate, calcium hydrogen phosphate, monosodium phosphate, potassium phosphate and potassium hydrogen phosphate; the source of calcium (calcium salt) is at least one of the following materials: calcium nitrate, calcium chloride, calcium bicarbonate, calcium sulfate, calcium bisulfate, calcium phosphate and calcium phosphate secondary; the source of sodium (sodium salt) is at least one of the following materials: sodium nitrate, sodium chloride, sodium carbonate, sodium bicarbonate, sodium sulfate, sodium bisulfate, sodium phosphate and sodium hydrogen phosphate; the source of magnesium (magnesium salt) is at least one of the following materials: magnesium nitrate, magnesium chloride, magnesium bicarbonate, magnesium sulfate and magnesium hydrogen sulfate; the source of aluminum (aluminum salt) is at least one of the following materials: aluminum nitrate, aluminum chloride, aluminum sulfate and aluminum sulfate hydrogen; the source of kalium (kalium salt) is at least one of the following materials: potassium nitrate, potassium chloride, potassium carbonate, potassium bicarbonate, potassium sulfate, potassium sulfate, potassium chlorate, sub-potassium chlorate, potassium phosphate and potassium hydrogen phosphate; the source of fluorine (fluorine salt) is at least one of the following materials: ammonium fluoride, ammonium hydrogen fluoride and hydrogen fluoride.

One solution for the optimized components is as follows: the silica salt (source of silicon) is tetraethyl orthosilicate, the phosphorus salt (source of phosphorus) is triethyl phosphate, the calcium salt (source of calcium) is calcium nitrate, the sodium salt (source of sodium) is sodium nitrate, the source of magnesium salt (source of magnesium) is magnesium nitrate, the aluminum salt (source of aluminum) is aluminum nitrate, the kalium salt (source of kalium) is potassium nitrate, the fluorine salt (source of fluorine) is ammonium fluoride.

The thermal spray technique in this invention could be either plasma spraying, or high velocity oxygen fuel spraying, or electric arc spraying, or thermal explosion spraying, or oxyacetylene flame thermal spraying. By employing different thermal spray techniques, the liquid precursor of bioactive glasses are sprayed onto the biomedical material substrates and form bioactive glass coating.

When plasma spraying is selected as the thermal spray technique, the liquid bioactive glass precursors can be directly injected into the high temperature area in plasma flame center in a radial direction, in the form of linear jet flow through a 50-200 micrometer small diameter catheter; the distance between the plasma gun and the biomedical materials substrate is 10-25 cm; the plasma spray power is 24-60 kW.

Figure 1:
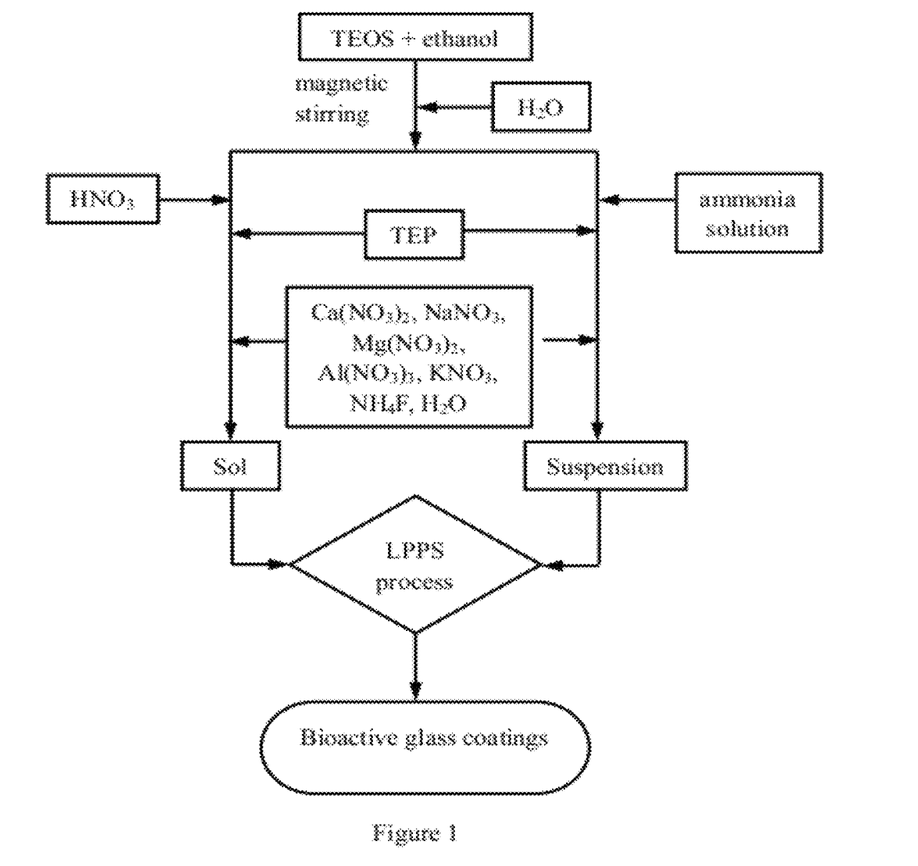
FIG. 1 schematic diagram of the process flow of the present invention

When liquid precursor plasma spraying is used in this invention to prepare bioactive glass coating, the procedures are carried out in accordance with process flow sheet in FIG. 1, including the following major steps:

(1) Preparation of the liquid bioactive glass precursor (2) Transportation and injection of the liquid bioactive glass precursor (3) Liquid precursor plasma spraying and the formation of the bioactive glass coating Specifically, the plasma spraying can be carried out by the following steps:

(1) Preparation of Liquid Precursor of Bioactive Glass a) Firstly, tetraethyl orthosilicate (TEOS), triethyl phosphate (TEP), calcium nitrate ($Ca(NO_3)_2.4H_2O$), sodium nitrate ($NaNO_3$), magnesium nitrate ($Mg(NO_3)_2.6H_2O$), aluminum nitrate ($Al(NO_3)_3.9H_2O$), potassium nitrate ($KNO_3$), and ammonium fluoride ($NH_4F$) are measured according to the composition of the bioactive glass, which is 30-60 wt % $SiO_2$, 1-40 wt % $P_2O_5$, 20-45 wt % CaO, 0-25 wt % $Na_2O$, 0-20 wt % MgO, 0-3 wt % $Al_2O_3$, 0-8 wt % $K_2O$, and 0-15 wt % $CaF_2$ in terms of the starting oxides, respectively. Ethyl alcohol and deionized water are measured according to the following molar ratios: TEOS:Ethyl alcohol (EtOH)=1:2-5, TEOS:$H_2O$=1:4-8. Deionized water are also measured according to the following mass ratios: $Ca(NO_3)_2.4H_2O$:$H_2O$=1:1-2, $NaNO_3$:$H_2O$=1:1-2, $Mg(NO_3)_2.6H_2O$:$H_2O$=1:1-2, $Al(NO_3)_3.9H_2O$:$H_2O$=1:1.5-2, $KNO_3$:$H_2O$=1:3-5, $NH_4F$:$H_2O$=1:1-2.

b) Mix the measured tetraethyl orthosilicate and ethyl alcohol under magnetic stirring with the rotation speed of 350-700 rpm. Add the deionized water after 5-10 min stirring.

c) Add $HNO_3$ to adjust the pH value to 1-3. Keep stirring for 10-20 minutes after the solution is completely pellucid.

Or:

d) Add $NH_3.H_2O$ to adjust the pH value to 9-11. Keep stirring for 10-20 minutes after the solution is completely muddy.

e) Add the triethyl phosphate and stirring for 5-10 minutes.

f) Add the measured calcium nitrate, sodium nitrate, magnesium nitrate, aluminum nitrate, potassium nitrate, ammonium fluoride to the deionized water. After being completely dissolved, they are added to the hydrolyzed sol or suspension. The bioactive glass precursor for plasma spray is manufactured after 20-30 min stirring.

(2) Transportation and Injection of the Liquid Precursor for Bioactive Glass

The electronic peristaltic pump is used as the driving power for the transportation of the liquid precursor. The rotating speed of the peristaltic pump is adjusted to 5-20 rpm. The bioactive glass precursor is transported, in a catheter with a diameter of 3-8 mm, to the injector near the plasma gun. The injection system uses small diameter tube with a 50-200 μm diameter, which injects the bioactive glass precursors into the high temperature area of the plasma flame center, in the form of linear jet flow.

(3) Liquid Precursor Plasma Spraying and the Formation of the Bioactive Glass Coating The plasma spray power is adjusted to 24-60 kW. The distance between the plasma gun and the biomedical materials substrate is 10-25 cm. The number of spray passes is 5-15. The liquid bioactive glass precursors are prepared through step (1), and transported and injected through step (2), and injected into the high temperature plasma flame at a certain speed. The liquid feedstock would undergo a series of process at high temperature: refining and breakup of droplets, evaporation, combustion, decomposition, melting, etc. Finally, feedstock materials are deposited and bioactive glass coating is formed on the biomedical materials substrate.

The following specific examples further describe the details of the invention. However, it should not be understood as the limitation of the invention. All amendments, replacement and change based on the idea of the present invention belong to the present invention.

Example 1

First of all, tetraethyl orthosilicate (TEOS), triethyl phosphate (TEP), calcium nitrate ($Ca(NO_3)_2.4H_2O$), sodium nitrate ($NaNO_3$) are measured according to the amount of starting oxides: $SiO_2$ 30 wt %, $P_2O_5$ 20 wt %, CaO 30 wt %, $Na_2O$ 20 wt %. Ethyl alcohol and deionized water are measured according to the following molar ratios: TEOS:EtOH=1:2, TEOS:$H_2O$=1:8. Deionized water are also measured according to the following mass ratios: $Ca(NO_3)_2.4H_2O$:$H_2O$=1:2, $NaNO_3$:$H_2O$=1:1. Mix the measured tetraethyl orthosilicate and ethyl alcohol under magnetic stirring with the rotation speed of 350 rpm. Add the deionized water after 5 min stirring. Add the nitric acid to adjust the pH value to 2. Keep stirring for 10 minutes after the solution is completely pellucid. Add the triethyl phosphate and keep stirring for 5 minutes. Add the measured calcium nitrate and sodium nitrate to the deionized water. After being completely dissolved, they are added to the hydrolyzed sol. The bioactive glass precursor for plasma spraying is prepared after 20 min stirring.

The electronic peristaltic pump is used as the driving power for the transportation of the liquid precursor. The rotation speed of the peristaltic pump is adjusted to 5 rpm. The bioactive glass precursor is transported, in a catheter with a diameter of 3 mm, to the injector near the plasma gun. The injection system uses a 50 μm small diameter tube, which injects the bioactive glass precursors into the high temperature area in plasma flame center, in the form of the linear jet flow.

The plasma spray power is adjusted to 24 kW. The distance between the plasma gun and the biomedical materials substrate is 10 cm. The number of spray passes is 5. The liquid bioactive glass precursors would undergo a series of process in high temperature plasma flame: combustion, evaporation, fast gelation, melting, and so on. Finally, feedstock materials are deposited and bioactive glass coating is formed on the biomedical titanium alloy substrate.

Example 2

First of all, tetraethyl orthosilicate (TEOS), triethyl phosphate (TEP), calcium nitrate ($Ca(NO_3)_2.4H_2O$), sodium nitrate ($NaNO_3$) are measured according to the amount of starting oxides: $SiO_2$ 45 wt %, $P_2O_5$ 6 wt %, CaO 24.5 wt %, $Na_2O$ 24.5 wt %. Ethyl alcohol and deionized water are measured according to the following molar ratios: TEOS:EtOH=1:3, TEOS:$H_2O$=1:7. Deionized water are also measured according to the following mass ratios: $Ca(NO_3)_2.4H_2O$:$H_2O$=1:1, $NaNO_3$:$H_2O$=1:2. Mix the measured tetraethyl orthosilicate and ethyl alcohol under magnetic stirring with the rotation speed of 400 rpm. Add the deionized water after 6 min stirring. Add the ammonia solution to adjust the pH value to 10. Keep stirring for 11 minutes after it becomes completely muddy. Add the triethyl phosphate and keep stirring for 6 minutes. Add the measured calcium nitrate and sodium nitrate to the deionized water. After being completely dissolved, they are added to the hydrolyzed suspension. The bioactive glass precursor for plasma spraying is prepared after 21 min stirring.

The electronic peristaltic pump is used as the driving power for the transportation of the liquid precursor. The rotation speed of the peristaltic pump is adjusted to 6 rpm. The bioactive glass precursor is transported, in a catheter with a diameter of 4 mm, to the injector near the plasma gun. The injection system uses a 60 μm small diameter tube, which injects the bioactive glass precursors into the high temperature area in plasma flame center, in the form of the linear jet flow.

The plasma spray power is adjusted to 36 kW. The distance between the plasma gun and the biomedical materials substrate is 12 cm. The number of spray passes is 10. The liquid bioactive glass precursors would undergo a series of process in high temperature plasma flame: combustion, evaporation, fast gelation, melting, and so on. Finally, feedstock materials are deposited and bioactive glass coating is formed on the biomedical titanium substrate.

Example 3

First of all, tetraethyl orthosilicate (TEOS), triethyl phosphate (TEP), calcium nitrate ($Ca(NO_3)_2.4H_2O$), sodium nitrate ($NaNO_3$), magnesium nitrate ($Mg(NO_3)_2.6H_2O$) are measured according to the amount of starting oxides: $SiO_2$ 50 wt %, $P_2O_5$ 5 wt %, CaO 20 wt %, $Na_2O$ 20 wt %, MgO 5 wt %. Ethyl alcohol and deionized water are measured according to the following molar ratios: TEOS:EtOH=1:4, TEOS:$H_2O$=1:4. Deionized water are also measured according to the following mass ratios: $Ca(NO_3)_2.4H_2O$:$H_2O$=1:1, $NaNO_3$:$H_2O$=1:1, $Mg(NO_3)_2.6H_2O$:$H_2O$=1:2. Mix the measured tetraethyl orthosilicate and ethyl alcohol under magnetic stirring with the rotation speed of 450 rpm. Add the deionized water after 7 min stirring. Add the nitric acid to adjust the pH value to 3. Keep stirring for 12 minutes after the solution is completely pellucid. Add the triethyl phosphate and keep stirring for 7 minutes. Add the measured calcium nitrate and sodium nitrate to the deionized water. After being completely dissolved, they are added to the hydrolyzed sol. The bioactive glass precursor for plasma spraying is prepared after 22 min stirring.

The electronic peristaltic pump is used as the driving power for the transportation of the liquid precursor. The rotation speed of the peristaltic pump is adjusted to 7 rpm. The bioactive glass precursor is transported, in a catheter with a diameter of 5 mm, to the injector near the plasma gun. The injection system uses a 70 μm small diameter tube, which injects the bioactive glass precursors into the high temperature area in plasma flame center, in the form of the linear jet flow.

The plasma spray power is adjusted to 40 kW. The distance between the plasma gun and the biomedical materials substrate is 14 cm. The number of spray passes is 15. The liquid bioactive glass precursors would undergo a series of process in high temperature plasma flame: combustion, evaporation, fast gelation, melting, and so on. Finally, feedstock materials are deposited and bioactive glass coating is formed on the biomedical stainless steel substrate.

Example 4

First of all, tetraethyl orthosilicate (TEOS), triethyl phosphate (TEP), calcium nitrate ($Ca(NO_3)_2.4H_2O$), sodium nitrate ($NaNO_3$) are measured according to the amount of starting oxides: $SiO_2$ 53.9 wt %, $P_2O_5$ 1.7 wt %, CaO 21.8 wt %, $Na_2O$ 22.6 wt %. Ethyl alcohol and deionized water are measured according to the following molar ratios: TEOS:EtOH=1:5, TEOS:$H_2O$=1:5. Deionized water are also measured according to the following mass ratios: $Ca(NO_3)_2.4H_2O$:$H_2O$=1:2, $NaNO_3$:$H_2O$=1:1. Mix the measured tetraethyl orthosilicate and ethyl alcohol under magnetic stirring with the rotation speed of 500 rpm. Add the deionized water after 8 min stirring. Add the ammonia solution to adjust the pH value to 9. Keep stirring for 13 minutes after it becomes completely muddy. Add the triethyl phosphate and keep stirring for 8 minutes. Add the measured calcium nitrate and sodium nitrate to the deionized water. After being completely dissolved, they are added to the hydrolyzed suspension. The bioactive glass precursor for plasma spraying is prepared after 23 min stirring.

The electronic peristaltic pump is used as the driving power for the transportation of the liquid precursor. The rotation speed of the peristaltic pump is adjusted to 8 rpm. The bioactive glass precursor is transported, in a catheter with a diameter of 6 mm, to the injector near the plasma gun. The injection system uses a 80 μm small diameter tube, which injects the bioactive glass precursors into the high temperature area in plasma flame center, in the form of the linear jet flow.

The plasma spray power is adjusted to 45 kW. The distance between the plasma gun and the biomedical materials substrate is 16 cm. The number of spray passes is 14. The liquid bioactive glass precursors would undergo a series of process in high temperature plasma flame: combustion, evaporation, fast gelation, melting, and so on. Finally, feedstock materials are deposited and bioactive glass coating is formed on the biomedical chromium alloy substrate.

Example 5

First of all, tetraethyl orthosilicate (TEOS), triethyl phosphate (TEP), calcium nitrate ($Ca(NO_3)_2.4H_2O$), sodium nitrate ($NaNO_3$), magnesium nitrate ($Mg(NO_3)_2.6H_2O$), potassium nitrate ($KNO_3$) are measured according to the amount of starting oxides: $SiO_2$ 46 wt %, $P_2O_5$ 1 wt %, CaO 27 wt %, $Na_2O$ 15 wt %, MgO 7 wt %, $K_2O$ 4 wt %. Ethyl alcohol and deionized water are measured according to the following molar ratios: TEOS:EtOH=1:4, TEOS:$H_2O$=1:4. Deionized water are also measured according to the following mass ratios: $Ca(NO_3)_2.4H_2O$:$H_2O$=1:1, $NaNO_3$:$H_2O$=1:2, $Mg(NO_3)_2.6H_2O$:$H_2O$=1:1, $KNO_3$:$H_2O$=1:5. Mix the measured tetraethyl orthosilicate and ethyl alcohol under magnetic stirring with the rotation speed of 550 rpm. Add the deionized water after 9 min stirring. Add the nitric acid to adjust the pH value to 1. Keep stirring for 14 minutes after the solution is completely pellucid. Add the triethyl phosphate and keep stirring for 9 minutes. Add the measured calcium nitrate and sodium nitrate to the deionized water. After being completely dissolved, they are added to the hydrolyzed sol. The bioactive glass precursor for plasma spraying is prepared after 24 min stirring.

The electronic peristaltic pump is used as the driving power for the transportation of the liquid precursor. The rotation speed of the peristaltic pump is adjusted to 9 rpm. The bioactive glass precursor is transported, in a catheter with a diameter of 7 mm, to the injector near the plasma gun. The injection system uses a 90 μm small diameter tube, which injects the bioactive glass precursors into the high temperature area in plasma flame center, in the form of the linear jet flow.

The plasma spray power is adjusted to 50 kW. The distance between the plasma gun and the biomedical materials substrate is 18 cm. The number of spray passes is 13. The liquid bioactive glass precursors would undergo a series of process in high temperature plasma flame: combustion, evaporation, fast gelation, melting, and so on. Finally, feedstock materials are deposited and bioactive glass coating is formed on the biomedical zirconia ceramic substrate.

Example 6

First of all, tetraethyl orthosilicate (TEOS), triethyl phosphate (TEP), calcium nitrate ($Ca(NO_3)_2 \cdot 4H_2O$), sodium nitrate ($NaNO_3$) are measured according to the amount of starting oxides: $SiO_2$ 60 wt %, $P_2O_5$ 4 wt %, CaO 20 wt %, $Na_2O$ 16 wt %. Ethyl alcohol and deionized water are measured according to the following molar ratios: TEOS:EtOH=1:3, TEOS:$H_2O$=1:5. Deionized water are also measured according to the following mass ratios: $Ca(NO_3)_2 \cdot 4H_2O:H_2O$=1:1, $NaNO_3:H_2O$=1:1. Mix the measured tetraethyl orthosilicate and ethyl alcohol under magnetic stirring with the rotation speed of 600 rpm. Add the deionized water after 10 min stirring. Add the ammonia solution to adjust the pH value to 11. Keep stirring for 15 minutes after it becomes completely muddy. Add the triethyl phosphate and keep stirring for 10 minutes. Add the measured calcium nitrate and sodium nitrate to the deionized water. After being completely dissolved, they are added to the hydrolyzed suspension. The bioactive glass precursor for plasma spraying is prepared after 25 min stirring.

The electronic peristaltic pump is used as the driving power for the transportation of the liquid precursor. The rotation speed of the peristaltic pump is adjusted to 10 rpm. The bioactive glass precursor is transported, in a catheter with a diameter of 8 mm, to the injector near the plasma gun. The injection system uses a 100 μm small diameter tube, which injects the bioactive glass precursors into the high temperature area in plasma flame center, in the form of the linear jet flow.

The plasma spray power is adjusted to 55 kW. The distance between the plasma gun and the biomedical materials substrate is 20 cm. The number of spray passes is 12. The liquid bioactive glass precursors would undergo a series of process in high temperature plasma flame: combustion, evaporation, fast gelation, melting, and so on. Finally, feedstock materials are deposited and bioactive glass coating is formed on the biomedical alumina ceramic substrate.

Example 7

First of all, tetraethyl orthosilicate (TEOS), triethyl phosphate (TEP), calcium nitrate ($Ca(NO_3)_2 \cdot 4H_2O$), sodium nitrate ($NaNO_3$), aluminum nitrate ($Al(NO_3)_3 \cdot 9H_2O$) are measured according to the amount of starting oxides: $SiO_2$ 40 wt %, $P_2O_5$ 2 wt %, CaO 30 wt %, $Na_2O$ 25 wt %, $Al_2O_3$ 3 wt %. Ethyl alcohol and deionized water are measured according to the following molar ratios: TEOS:EtOH=1:2, TEOS:$H_2O$=1:6. Deionized water are also measured according to the following mass ratios: $Ca(NO_3)_2 \cdot 4H_2O:H_2O$=1:1, $NaNO_3:H_2O$=1:1, $Al(NO_3)_3 \cdot 9H_2O: H_2O$=1:2. Mix the measured tetraethyl orthosilicate and ethyl alcohol under magnetic stirring with the rotation speed of 450 rpm. Add the deionized water after 9 min stirring. Add the nitric acid to adjust the pH value to 1. Keep stirring for 16 minutes after the solution is completely pellucid. Add the triethyl phosphate and keep stirring for 9 minutes. Add the measured calcium nitrate and sodium nitrate to the deionized water. After being completely dissolved, they are added to the hydrolyzed sol. The bioactive glass precursor for plasma spraying is prepared after 26 min stirring.

The electronic peristaltic pump is used as the driving power for the transportation of the liquid precursor. The rotation speed of the peristaltic pump is adjusted to 12 rpm. The bioactive glass precursor is transported, in a catheter with a diameter of 7 mm, to the injector near the plasma gun. The injection system uses a 120 μm small diameter tube, which injects the bioactive glass precursors into the high temperature area in plasma flame center, in the form of the linear jet flow.

The plasma spray power is adjusted to 60 kW. The distance between the plasma gun and the biomedical materials substrate is 21 cm. The number of spray passes is 11. The liquid bioactive glass precursors would undergo a series of process in high temperature plasma flame: combustion, evaporation, fast gelation, melting, and so on. Finally, feedstock materials are deposited and bioactive glass coating is formed on the biomedical titanium substrate.

Example 8

First of all, tetraethyl orthosilicate (TEOS), triethyl phosphate (TEP), calcium nitrate ($Ca(NO_3)_2 \cdot 4H_2O$), magnesium nitrate ($Mg(NO_3)_2 \cdot 6H_2O$), and ammonium fluoride ($NH_4F$) are measured according to the amount of starting oxides: $SiO_2$ 30 wt %, $P_2O_5$ 40 wt %, CaO 26 wt %, MgO 3 wt %, $CaF_2$ 1 wt %. Ethyl alcohol and deionized water are measured according to the following molar ratios: TEOS:EtOH=1:3, TEOS:$H_2O$=1:7. Deionized water are also measured according to the following mass ratios: $Ca(NO_3)_2 \cdot 4H_2O:H_2O$=1:1, $Mg(NO_3)_2 \cdot 6H_2O:H_2O$=1:2, $NH_4F:H_2O$=1:2. Mix the measured tetraethyl orthosilicate and ethyl alcohol under magnetic stirring with the rotation speed of 700 rpm. Add the deionized water after 8 min stirring. Add the ammonia solution to adjust the pH value to 9. Keep stirring for 17 minutes after it becomes completely muddy. Add the triethyl phosphate and keep stirring for 8 minutes. Add the measured calcium nitrate and sodium nitrate to the deionized water. After being completely dissolved, they are added to the hydrolyzed suspension. The bioactive glass precursor for plasma spraying is prepared after 27 min stirring.

The electronic peristaltic pump is used as the driving power for the transportation of the liquid precursor. The rotation speed of the peristaltic pump is adjusted to 14 rpm. The bioactive glass precursor is transported, in a catheter with a diameter of 6 mm, to the injector near the plasma gun. The injection system uses a 140 μm small diameter tube, which injects the bioactive glass precursors into the high temperature area in plasma flame center, in the form of the linear jet flow.

The plasma spray power is adjusted to 35 kW. The distance between the plasma gun and the biomedical materials substrate is 23 cm. The number of spray passes is 9. The liquid bioactive glass precursors would undergo a series of process in high temperature plasma flame: combustion, evaporation, fast gelation, melting, and so on. Finally, feedstock materials are deposited and bioactive glass coating is formed on the biomedical titanium alloy substrate.

Example 9

First of all, tetraethyl orthosilicate (TEOS), triethyl phosphate (TEP), calcium nitrate ($Ca(NO_3)_2 \cdot 4H_2O$), magnesium nitrate ($Mg(NO_3)_2 \cdot 6H_2O$), and ammonium fluoride ($NH_4F$) are measured according to the amount of starting oxides: $SiO_2$ 34 wt %, $P_2O_5$ 16.2 wt %, CaO 44.7 wt %, MgO 4.6 wt %, $CaF_2$ 0.5 wt %. Ethyl alcohol and deionized water are measured according to the following molar ratios: TEOS:EtOH=1:4, TEOS:$H_2O$=1:8. Deionized water are also measured according to the following mass ratios: $Ca(NO_3)_2 \cdot 4H_2O:H_2O$=1:1, $Mg(NO_3)_2 \cdot 6H_2O:H_2O$=1:1, $NH_4F:H_2O=1:2$. Mix the measured tetraethyl orthosilicate and ethyl alcohol under magnetic stirring with the rotation speed of 650 rpm. Add the deionized water after 7 min stirring. Add the nitric acid to adjust the pH value to 2. Keep stirring for 18 minutes after the solution is completely pellucid. Add the triethyl phosphate and keep stirring for 7 minutes. Add the measured calcium nitrate and sodium nitrate to the deionized water. After being completely dissolved, they are added to the hydrolyzed sol. The bioactive glass precursor for plasma spraying is prepared after 28 min stirring.

The electronic peristaltic pump is used as the driving power for the transportation of the liquid precursor. The rotation speed of the peristaltic pump is adjusted to 16 rpm. The bioactive glass precursor is transported, in a catheter with a diameter of 5 mm, to the injector near the plasma gun. The injection system uses a 160 μm small diameter tube, which injects the bioactive glass precursors into the high temperature area in plasma flame center, in the form of the linear jet flow.

The plasma spray power is adjusted to 38 kW. The distance between the plasma gun and the biomedical materials substrate is 25 cm. The number of spray passes is 8. The liquid bioactive glass precursors would undergo a series of process in high temperature plasma flame: combustion, evaporation, fast gelation, melting, and so on. Finally, feedstock materials are deposited and bioactive glass coating is formed on the biomedical stainless steel substrate.

Example 10

First of all, tetraethyl orthosilicate (TEOS), triethyl phosphate (TEP), calcium nitrate ($Ca(NO_3)_2.4H_2O$), sodium nitrate ($NaNO_3$), magnesium nitrate ($Mg(NO_3)_2.6H_2O$), and potassium nitrate ($KNO_3$) are measured according to the amount of starting oxides: $SiO_2$ 40 wt %, $P_2O_5$ 10 wt %, CaO 30 wt %, NaO 5 wt %, MgO 3 wt %, $K_2O$ 2 wt %. Ethyl alcohol and deionized water are measured according to the following molar ratios: $TEOS:EtOH=1:5$, $TEOS:H_2O=1:7$. Deionized water are also measured according to the following mass ratios: $Ca(NO_3)_2.4H_2O:H_2O=1:1$, $NaNO_3:H_2O=1:2$, $Mg(NO_3)_2:H_2O=1:2$, $KNO_3:H_2O=1:3$. Mix the measured tetraethyl orthosilicate and ethyl alcohol under magnetic stirring with the rotation speed of 600 rpm. Add the deionized water after 6 min stirring. Add the ammonia solution to adjust the pH value to 10. Keep stirring for 19 minutes after it becomes completely muddy. Add the triethyl phosphate and keep stirring for 6 minutes. Add the measured calcium nitrate and sodium nitrate to the deionized water. After being completely dissolved, they are added to the hydrolyzed suspension. The bioactive glass precursor for plasma spraying is prepared after 29 min stirring.

The electronic peristaltic pump is used as the driving power for the transportation of the liquid precursor. The rotation speed of the peristaltic pump is adjusted to 18 rpm. The bioactive glass precursor is transported, in a catheter with a diameter of 4 mm, to the injector near the plasma gun. The injection system uses a 180 μm small diameter tube, which injects the bioactive glass precursors into the high temperature area in plasma flame center, in the form of the linear jet flow.

The plasma spray power is adjusted to 42 kW. The distance between the plasma gun and the biomedical materials substrate is 11 cm. The number of spray passes is 7. The liquid bioactive glass precursors would undergo a series of process in high temperature plasma flame: combustion, evaporation, fast gelation, melting, and so on. Finally, feedstock materials are deposited and bioactive glass coating is formed on the biomedical chromium alloy substrate.

Example 11

First of all, tetraethyl orthosilicate (TEOS), triethyl phosphate (TEP), calcium nitrate ($Ca(NO_3)_2.4H_2O$), sodium nitrate ($NaNO_3$), magnesium nitrate ($Mg(NO_3)_2.6H_2O$), potassium nitrate ($KNO_3$), and ammonium fluoride ($NH_4F$) are measured according to the amount of starting oxides: $SiO_2$ 44.3 wt %, $P_2O_5$ 11.2 wt %, CaO 31.9 wt %, $Na_2O$ 4.6 wt %, MgO 2.8 wt %, $K_2O$ 0.2 wt %, $CaF_2$ 5 wt %. Ethyl alcohol and deionized water are measured according to the following molar ratios: $TEOS:EtOH=1:4$, $TEOS:H_2O=1:6$. Deionized water are also measured according to the following mass ratios: $Ca(NO_3)_2.4H_2O:H_2O=1:1$, $NaNO_3:H_2O=1:2$, $Mg(NO_3)_2.6H_2O:H_2O=1:1$, $KNO_3:H_2O=1:5$, $NH_4F:H_2O=1:1$. Mix the measured tetraethyl orthosilicate and ethyl alcohol under magnetic stirring with the rotation speed of 550 rpm. Add the deionized water after 5 min stirring. Add the nitric acid to adjust the pH value to 3. Keep stirring for 20 minutes after the solution is completely pellucid. Add the triethyl phosphate and keep stirring for 5 minutes. Add the measured calcium nitrate and sodium nitrate to the deionized water. After being completely dissolved, they are added to the hydrolyzed sol. The bioactive glass precursor for plasma spraying is prepared after 30 min stirring.

The electronic peristaltic pump is used as the driving power for the transportation of the liquid precursor. The rotation speed of the peristaltic pump is adjusted to 20 rpm. The bioactive glass precursor is transported, in a catheter with a diameter of 3 mm, to the injector near the plasma gun. The injection system uses a 200 μm small diameter tube, which injects the bioactive glass precursors into the high temperature area in plasma flame center, in the form of the linear jet flow.

The plasma spray power is adjusted to 30 kW. The distance between the plasma gun and the biomedical materials substrate is 13 cm. The number of spray passes is 6. The liquid bioactive glass precursors would undergo a series of process in high temperature plasma flame: combustion, evaporation, fast gelation, melting, and so on. Finally, feedstock materials are deposited and bioactive glass coating is formed on the biomedical zirconia ceramic substrate.

Example 12

First of all, tetraethyl orthosilicate (TEOS), triethyl phosphate (TEP), calcium nitrate ($Ca(NO_3)_2.4H_2O$), sodium nitrate ($NaNO_3$), potassium nitrate ($KNO_3$), and ammonium fluoride ($NH_4F$) are measured according to the amount of starting oxides: $SiO_2$ 35 wt %, $P_2O_5$ 7 wt %, CaO 20 wt %, NaO 15 wt %, $K_2O$ 8 wt %, $CaF_2$ 15 wt %. Ethyl alcohol and deionized water are measured according to the following molar ratios: $TEOS:EtOH=1:3$, $TEOS:H_2O=1:5$. Deionized water are also measured according to the following mass ratios: $Ca(NO_3)_2.4H_2O:H_2O=1:2$, $NaNO_3:H_2O=1:1$, $KNO_3:H_2O=1:4$, $NH_4F:H_2O=1:2$. Mix the measured tetraethyl orthosilicate and ethyl alcohol under magnetic stirring with the rotation speed of 500 rpm. Add the deionized water after 6 min stirring. Add the ammonia solution to adjust the pH value to 11. Keep stirring for 15 minutes after it becomes completely muddy. Add the triethyl phosphate and keep stirring for 6 minutes. Add the measured calcium nitrate and sodium nitrate to the deionized water. After being completely dissolved, they are added to the hydrolyzed suspension. The bioactive glass precursor for plasma spraying is prepared after 29 min stirring.

The electronic peristaltic pump is used as the driving power for the transportation of the liquid precursor. The rotation speed of the peristaltic pump is adjusted to 17 rpm. The bioactive glass precursor is transported, in a catheter with a diameter of 4 mm, to the injector near the plasma gun. The injection system uses a 110 μm small diameter tube, which injects the bioactive glass precursors into the high temperature area in plasma flame center, in the form of the linear jet flow.

The plasma spray power is adjusted to 48 kW. The distance between the plasma gun and the biomedical materials substrate is 15 cm. The number of spray passes is 5. The liquid bioactive glass precursors would undergo a series of process in high temperature plasma flame: combustion, evaporation, fast gelation, melting, and so on. Finally, feedstock materials are deposited and bioactive glass coating is formed on the biomedical alumina ceramic substrate.

Example 13

Figure 2:
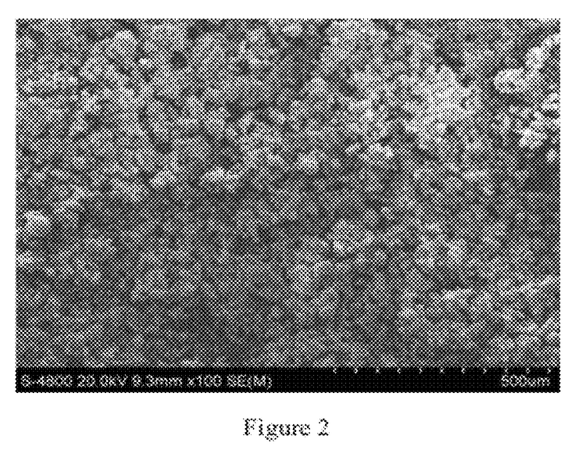
FIG. 2 scanning electron microscope (SEM) picture of the bioactive glass coating synthesized according to example 2 at a magnification of 100×.
Figure 3:
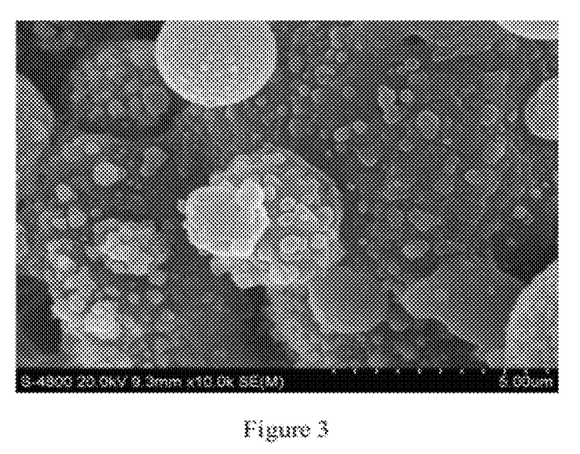
FIG. 3 SEM picture of the bioactive glass coating synthesized according to example 2 at a magnification of 100,000×.

The bioactive glass coatings synthesized in example 2 was examined under the SEM. The results showed that the synthesized coating had a uniform structure, tight adhesion to the substrate, and the coating thickness is about 100-300 μm (the SEM micrograph at 100× is shown in FIG. 2, and the SEM micrograph at 100000× is shown in FIG. 3).

Figure 4:
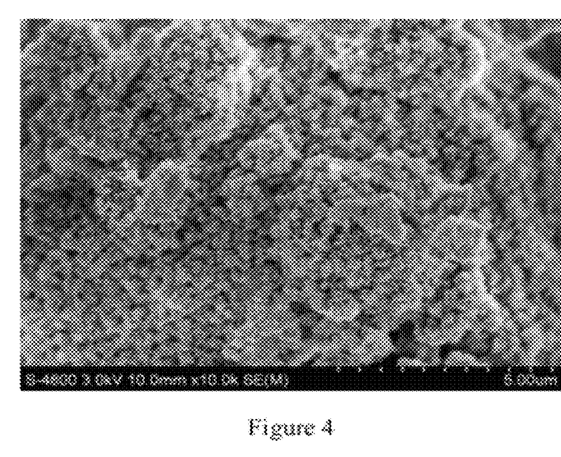
FIG. 4 SEM picture of the bioactive glass coating synthesized according to example 2, after immersion in simulated body fluid (SBF) for 7 days.

The above sample synthesized in example 2 was then soaked into SBF solution for 7 days, and the soaked sample was examined using SEM (see FIG. 4). The image showed that the surface were completely covered by the apatite layer (HA) after 7 day soaking, indicating good bioactivity of the bioactive glass coating prepared by the liquid precursor plasma spraying process.

Figure 5:
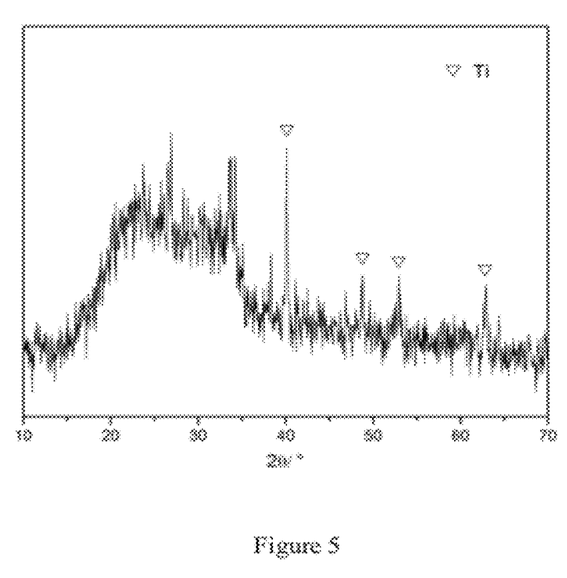
FIG. 5 X-ray diffraction (XRD) pattern of the bioactive glass coating synthesized according to example 2. In this pattern, the crystallization peaks are the crystalline phase of titanium (Ti) from substrate. The coating is mainly composed of amorphous phase.

The bioactive glass coating synthesized in example 2 was examined under the XRD (see FIG. 5). The results showed that the synthesized coating had no crystalline peaks except for these from the Ti substrate, indicating that the coating were mainly composed of amorphous phase.

Figure 6:
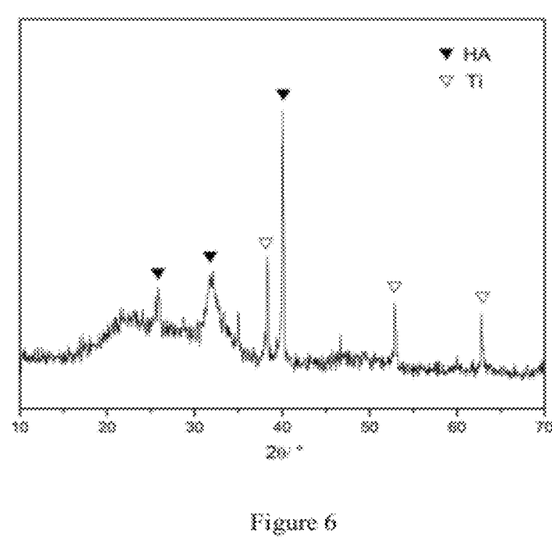
FIG. 6 XRD pattern of the bioactive glass coating synthesized according to example 2, after immersion in SBF for 7 days.

The bioactive glass coating synthesized in example 2 and soked in SBF solution for 7 days was examined under the XRD (see FIG. 6). The results showed that the synthesized coating had HA crystalline peaks beside the peaks from the Ti substrate, which is in agreement with the SEM observations. This further indicates that the bioactive glass coating prepared by the liquid precursor plasma spraying process has good bioactivity.

The invention claimed is:

1. A method for preparing bioactive glass coating, said method comprising the following steps:
   a. preparing a liquid bioactive glass precursor by combining deionized water, ethyl alcohol and salts of silicon, phosphorus, calcium, sodium, magnesium, aluminum, potassium, and fluorine, wherein the salts are measured according to the following starting amounts of compounds of the bioactive glass coating such that the bioactive glass coating comprises: 30-60 wt % $SiO_2$, 1-40 wt % $P_2O_5$, 20-45 wt % CaO, 0-25% $Na_2O$, 0-20 wt % MgO, 0-3 wt % $Al_2O_3$, 0-8 wt % $K_2O$ and 0-15 wt % $CaF_2$; and
   b. thermal spraying the liquid bioactive glass precursor on a biomedical material substrate to form the bioactive glass coating.

2. The method of claim 1, wherein the liquid bioactive glass precursor, comprises:
   sources (salts) of Silicon, Phosphorus, Calcium, Sodium, Magnesium, Aluminum, Potassium and Fluorine measured according to amounts of starting oxides: $SiO_2$ 30-60 wt %, $P_2O_5$ 1-40 wt %, CaO 20-45 wt %, $Na_2O$ 0-25 wt %, MgO 0-20 wt %, $Al_2O_3$ 0-3 wt %, $K_2O$ 0-8 wt %, $CaF_2$ 0-15 wt %;
   Ethyl alcohol and Deionized water measured according to molar ratios of Silicon:Ethyl alcohol=1:2-5, and Silicon:$H_2O$=1:4-8, respectively, wherein the Deionized water is also measured according to mass ratios of calcium:$H_2O$=1:1-2, sodium:$H_2O$=1:1-2, magnesium:$H_2O$=1:1-2, aluminum:$H_2O$=1:1.5-2, potassium:$H_2O$=1:3-5, and fluorine:$H_2O$=1:1-2, respectively.

3. The method of claim 2, wherein the bioactive glass precursor is prepared using the following sequential steps:
   (1) Mixing the silicon salt and ethyl alcohol and stirring them uniformly, and then adding the deionized water;
   (2) Adjusting the pH value to 1-3, hydrolyzing the silicon salt to form a sol, and uniformly stirring the sol after it becomes completely pellucid;
   (3) Adding of phosphorus to the sol and stirring the sol;
   (4) Completely dissolving the salts of calcium, sodium, magnesium, aluminum, potassium and fluorine in the deionized water to provide a solution, which is then added to the sol to provide the liquid bioactive glass precursor after uniform stirring.

4. The method of claim 2, wherein the bioactive glass basic precursor is prepared using the following sequential steps:
   (1) Mixing the silicon salt and ethyl alcohol and stirring them uniformly, and then adding the deionized water;
   (2) Adjusting a pH value to 9-11, hydrolyzing the silicon salt to form a suspension, stirring the suspension uniformly after it becomes completely muddy;
   (3) Adding the phosphorus salt followed by 5-10 min stirring;
   (4) Completely dissolving the salts of calcium, sodium, magnesium, aluminum, potassium and fluorine in the deionized water to provide a solution, which is then added to the suspension to provide the liquid bioactive glass precursor after uniform stirring.

5. The method of claim 2, wherein:
   the source of silicon is at least one of the following materials: tetraethyl orthosilicate, trimethyl silanol, triethyl silanol and silicon tetrachloride;
   the source of phosphorus is at least one of the following materials: triethyl phosphate, calcium phosphate, sodium phosphate, calcium hydrogen phosphate, monosodium phosphate, potassium phosphate and potassium hydrogen phosphate;
   the source of calcium is at least one of the following materials: calcium nitrate, calcium chloride, calcium bicarbonate, calcium sulfate, calcium bisulfate, calcium phosphate and calcium phosphate secondary;
   the source of sodium is at least one of the following materials: sodium nitrate, sodium chloride, sodium carbonate, sodium bicarbonate, sodium sulfate, sodium bisulfate, sodium phosphate and sodium hydrogen phosphate;
   the source of magnesium is at least one of the following materials: magnesium nitrate, magnesium chloride, magnesium bicarbonate, magnesium sulfate and magnesium hydrogen sulfate;

the source of aluminum is at least one of the following materials: aluminum nitrate, aluminum chloride, aluminum sulfate and aluminum sulfate hydrogen;

the source of potassium is at least one of the following materials: potassium nitrate, potassium chloride, potassium carbonate, potassium bicarbonate, potassium sulfate, potassium sulfate, potassium chlorate, sub-potassium chlorate, potassium phosphate and potassium hydrogen phosphate; and the source of fluorine is at least one of the following materials: ammonium fluoride, ammonium hydrogen fluoride and hydrogen fluoride.

6. The method of claim 5, wherein the source of silicon is tetraethyl orthosilicate, the source of phosphorus is triethyl phosphate, the source of calcium is calcium nitrate, the source of sodium is sodium nitrate, the source of magnesium is magnesium nitrate, the source of aluminum is aluminum nitrate, the source of potassium is potassium nitrate, and the source of fluorine is ammonium fluoride.

7. The method of claim 1, wherein the thermal spraying is plasma spraying, high velocity oxygen fuel spraying, electric arc spraying, thermal explosion spraying, or oxyacetylene flame thermal spraying.

8. The method of claim 7, wherein the liquid bioactive glass precursors is directly injected into a plasma flame center in a radial direction, in the form of linear jet flow through a 50-200 micrometer small diameter catheter.

9. The method of claim 7, wherein a distance between a plasma gun and the biomedical materials substrate is 10-25 cm.

10. The method of claim 7, wherein a plasma spray power is 24-60 kW.

11. The method of claim 1, wherein the biomedical material substrate comprises a biomedical titanium, a biomedical titanium alloy, a biomedical stainless steel, a biomedical Co-based alloy, another biomedical metal, a biomedical metallic composite, a biomedical ceramic, or a biomedical ceramic composite.

* * * * *